United States Patent
Henderson et al.

(10) Patent No.: US 10,722,524 B2
(45) Date of Patent: *Jul. 28, 2020

(54) COMPOSITIONS COMPRISING HYDROXYTYROSOL AND BOSWELLIC ACID

(71) Applicant: Nutramax Laboratories, Inc., Lancaster, SC (US)

(72) Inventors: Todd Henderson, Lancaster, SC (US); David Griffin, Forest Hill, MD (US)

(73) Assignee: NUTRAMAX LABORATORIES, INC., Lancaster, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,672

(22) Filed: Apr. 12, 2019

(65) Prior Publication Data

US 2019/0231796 A1 Aug. 1, 2019

Related U.S. Application Data

(63) Continuation of application No. 15/494,022, filed on Apr. 21, 2017, now Pat. No. 10,342,802, which is a continuation of application No. PCT/US2017/028857, filed on Apr. 21, 2017.

(60) Provisional application No. 62/403,807, filed on Oct. 4, 2016.

(51) Int. Cl.
| | |
|---|---|
| *A61K 31/56* | (2006.01) |
| *A61K 31/05* | (2006.01) |
| *A61K 36/63* | (2006.01) |
| *A61K 36/324* | (2006.01) |

(52) U.S. Cl.
CPC ............ *A61K 31/56* (2013.01); *A61K 31/05* (2013.01); *A61K 36/324* (2013.01); *A61K 36/63* (2013.01)

(58) Field of Classification Search
CPC ...... A61K 31/05; A61K 31/56; A61K 36/324; A61K 36/63
See application file for complete search history.

(56) References Cited

U.S. PATENT DOCUMENTS 8,841,264 B2 * 9/2014 Raederstorff .......... A61K 31/05
514/32

FOREIGN PATENT DOCUMENTS

WO 2006-020588 A1 2/2006

OTHER PUBLICATIONS

International Preliminary Report on Patentability and Written Opinion of the International Searching Authority for PCT/US2017/028857 dated Apr. 18, 2019.

* cited by examiner

*Primary Examiner* — Sarah Pihonak
(74) *Attorney, Agent, or Firm* — King & Schlicki, PLLC

(57) ABSTRACT

Compositions are described including a synergistic combination of hydroxytyrosol and 3-O-acetyl-11-keto-β-boswellic acid. The hydroxytyrosol may be sourced from an olive extract and the 3-O-acetyl-11-keto-β-boswellic acid may be sourced from a *Boswellia serrata* extract. The compositions may be formulated for oral administration to a mammalian or an avian subject. Methods for treating, repairing, or reducing damage to connective tissue caused by one or more inflammatory mediators and for reducing levels of one or more inflammatory mediators in connective tissue are provided, the methods comprising orally administering the compositions to a subject in need thereof.

10 Claims, 3 Drawing Sheets

COMPOSITIONS COMPRISING HYDROXYTYROSOL AND BOSWELLIC ACID

This application claims the benefit of priority of U.S. Continuation patent application. Ser. No. 15/494,022 filed on Apr. 21, 2017, now U.S. Pat. No. 10,342,802, which in turn claims priority to PCT Patent Application Serial No. PCT/US17/28857 filed on Apr. 21, 2017, which in turn claims priority to U.S. Provisional Patent Application Ser. No. 62/403,807 filed on Oct. 4, 2016, the entirety of the contents of each of which are incorporated by reference herein.

TECHNICAL FIELD

The present invention provides methods comprising administration of: (i) 3-O-acetyl-11-keto-β-boswellic acid (AKBA) and (ii) hydroxytyrosol, to a mammalian or an avian subject. The present invention also provides orally administrable compositions comprising AKBA and hydroxytyrosol.

BACKGROUND

Connective tissue is the structural framework of cartilage, bone, synovium, ligament, meniscus, and tendon in articulating joints. Components of connective tissue are produced by resident cells and then secreted to form the extracellular matrix (ECM) characteristics of the tissue. In addition to serving as structural framework, the ECM also plays a critical role in cell communication and function. In articular cartilage, chondrocytes are aligned in a distinct pattern within the type II collagen ECM framework. Bone forming osteoblasts and osteocytes, as well as bone resorbing osteoclasts, are organized in mineralized type I collagen ECM. The few fibroblast-like and macrophage-like cells in the synovium are also held in place by ECM. Similarly, tenocytes and ligament cells are assembled together within the ECM. The synthesis and breakdown of connective tissue ECM is controlled by a network of regulatory molecules which are also produced by the resident tissue cells. This network includes growth factors and a wide array of molecules known as pro-inflammatory mediators.

They include cytokines, chemokines, prostaglandins and nitric oxide. These molecules exhibit many biological activities. They can induce cell proliferation or cell death. These substances can also induce anabolic pathways for production of ECM or induce catabolic enzymes that can break down the ECM. Under physiological conditions, cell survival or death, the production or breakdown of connective tissue ECM is tightly controlled to maintain balanced homeostasis. The production and function of regulatory molecules is modulated by many factors including mechanical forces, physical factors such as temperature and pH, chemicals, microbes and their products. Under certain conditions, these factors can elicit excessive and untimely production of regulatory molecules leading to irreparable tissue damage, loss of function and death.

Tissues react to mechanical, physical, chemical insults and infection by an inflammatory response. The inflammation process is known to lead to recovery, to healing, defense against infection and is usually life preserving. The inflammatory response in humans and animals consists of two phases. The initial phase is characterized by the local synthesis of pro-inflammatory mediators such prostaglandins and leukotrienes. They are derived from arachidonic acid through the action of cyclooxygenases and lipoxygenases. These pro-inflammatory mediators increase local blood flow and enhance the permeability of endothelial cells to allow leukocyte recruitment and accumulation. Other pro-inflammatory mediators which are subsequently produced include cytokines (Interleukin-1 beta (IL-1 β), tumor necrosis factor alpha (TNF-α)), chemokines (IL-8), and nitric oxide. In the second phase, the resolution phase, prostaglandins generated during the initial phase activate enzymatic pathways along which arachidonic acid is converted to chemical mediators with anti-inflammatory properties. It has been reported that prostaglandin $E_2$ ($PGE_2$) activates the expression of 15-lipoxygenase which generates anti-inflammatory lipoxins from arachidonic acid. Thus, the resolution of inflammation is driven by the pro-inflammatory response. These studies indicate that the initiation, progression and termination of the inflammation process are tightly controlled. Prolonged, exaggerated inflammation has been associated with many disorders including osteoarthritis (OA), rheumatoid arthritis (RA), Alzheimer's disease, and cardiovascular disease.

In joint tissues, chondrocytes, synoviocytes, osteoblasts, osteoclasts, ligament cells, and tenocytes produce a wide array of pro-inflammatory mediators. Among these is $PGE_2$, which is known to play a regulatory role by inducing the production of other mediators including cytokines, nitric oxide, and connective tissue degrading metalloproteinase (MMP) enzymes. Due to its ability to induce metalloproteinases (MMPs), PGE2 contributes to the breakdown of cartilage ECM. In addition, $PGE_2$ promotes bone resorption and osteophyte formation. $PGE_2$ sensitizes nociceptors on peripheral nerve endings, thereby contributing to the development of inflammatory pain. $PGE_2$ levels are locally regulated by the cyclooxygenase-2 (COX-2) enzyme. In pathologic conditions such as osteoarthritis, COX-2 expression is up-regulated with a concomitant increase in PGE2 production.

TNF-α is a major mediator of inflammation and plays an important role in tissue regeneration/expansion and destruction during inflammation. In a normal state, inflammation is well regulated by these factors. That is, after these factors cause inflammation with the concomitant induction of immune responses, their levels decrease to a normal state. However, deregulated TNF-α production causes chronic inflammation, which is directly associated with a variety of diseases such as arthritis.

While inflammation is a crucial immunological process necessary to resolve tissue injury or infection, the chronic release of pro-inflammatory mediators like IL-1β and TNF-α can continue to induce production of additional inflammatory mediators. If levels do not return to a normal state, the dysregulated production of TNF-α can potentially lead to a detrimental pathophysiological process, including osteoarthritis (OA).

TNF-α plays a key role in the initiation of the inflammatory process. TNF-α is produced by a variety of cells in the joint, namely chondrocytes, osteoblasts, cells in the synovial membrane, and resident immune cells in the joint, or those that infiltrate the joint during the inflammatory response. Increased levels of TNF-α are detected in synovial fluid, synovial membrane, cartilage, and subchondral bone of those with osteoarthritis.

TNF-α along with IL-1β are capable of inducing Nuclear factor-kappa B (NF-κB), the master regulator of the inflammatory response. TNF-α induces the production of $PGE_2$ by increasing the production of the key enzymes involved in its synthesis, including COX-2, microsomal PGE synthase (mPGES-1), and soluble Phospholipase A2 (sPLA2). Additionally, TNF-α induces the production of inducible nitric oxide synthase (iNOS) resulting in an increase in nitric oxide (NO) levels. The production of other cytokines, including IL-6, IL-17 and IL-18 and the chemokine IL-8 are positively modulated by TNF-α. In combination, the production of these pro-inflammatory mediators—prostaglandins, NO, cytokines and chemokines—ultimately results the in the breakdown of cartilage associated with osteoarthritis.

TNF-α is capable of inhibiting the production of two key components of the extra cellular matrix—aggrecan and type II collagen. Further, TNF-α induces the expression of aggrecanases ADAMTS4 and ADAMTS-5, enzymes that degrade aggrecan. These two actions combined disrupt the normal biochemical balance between synthesis and degradation of the cartilage matrix in the joint, ultimately resulting in cartilage degeneration. TNF-α has also been shown to play a role in mitochondrial dysfunction, decreased ATP production and apoptosis further contributing to cartilage destruction. While TNF-α plays a central role in initiating the essential immune response to injury and infection, the deleterious effects that it triggers when dysregulated make TNF-α a target for development of inflammation management products.

The role of other tissues in the inflammation process is also well established. Inflammation of the synovial membrane is now recognized to be a key event in cartilage degradation in osteoarthritis, particularly during the early stages of the disease. Synovitis is characterized by activation of resident macrophage-like cells and fibroblast-like cells in the synovial membrane which leads to production of excessive amounts of pro-inflammatory mediators including TNF-α, IL-1 β, and PGE$_2$. Recent evidence suggests that synovial macrophages are the main source of the cytokines in the earliest stages of osteoarthritis and that they are important contributors to the cartilage damage in osteoarthritis throughout the course of the disease. Cytokines also induce production of PGE$_2$ and active metalloproteinases (MMPs). It is now well accepted that these mediators control the balance between ECM destruction and repair, which has made these molecules preferred targets for therapeutic intervention. Other tissues in the joint such as the subchondral bone also produce pro-inflammatory mediators that modulate joint health.

In addition to pro-inflammatory mediators such as cytokines and prostaglandins, reactive oxygen species (ROS) have also been implicated in joint degeneration observed in osteoarthritis. Oxidative stress induced by ROS such as nitric oxide and hydrogen peroxide has been shown to cause chondrocyte apoptosis and cartilage ECM breakdown. Moreover, ROS have been reported to activate signal transduction pathways that lead to an increased production of pro-inflammatory mediators including cytokines and prostaglandins. Studies in vitro have demonstrated a linkage between the pathways involved in the production of ROS and pro-inflammatory mediators. These studies support the notion that agents capable of inhibiting both oxidative stress and inflammation pathways would be particularly useful in the modulation of inflammation.

The central role of COX-2 and PGE$_2$ in the pathophysiology of osteoarthritis is reflected in the widespread use of selective COX-2 inhibitors and a variety of non-selective non-steroidal anti-inflammatory drugs (NSAIDs) for the treatment of the disorder. However, prolonged administration of these drugs has adverse side effects, including gastrointestinal pathologies and disruption of cartilage proteoglycan metabolism. Studies in human and animal models have demonstrated impaired bone healing and repair with the use of COX inhibitors. Therefore, there is a need for alternative treatments for the management of inflammation that do not center on the use of NSAIDs to inhibit the production of PGE$_2$ and other pro-inflammatory mediators, including TNF-α.

Among the drugs developed thus far for targeting TNF-α are Infliximab (a chimeric monoclonal antibody against human TNF), Adalimumab (a fully human monoclonal antibody), Etanercept (a dimeric TNFRII (p75) fusion protein linked to the Fc portion of human IgG), Golimumab, CDP571, and Thalidomide. However, in addition to inhibiting the positive functions of TNF-α, these drugs may elicit unwanted outcomes including lymphoma development and infection. There is therefore a need for therapeutic agents that regulate the excessive reactive oxygen species generation and cell death which is induced by TNF-α without blocking the positive physiological functions of TNF-α.

SUMMARY

In accordance with the purposes and benefits described herein, in one aspect of the present disclosure a composition is provided comprising a combination of hydroxytyrosol and 3-O-acetyl-11-keto-β-boswellic acid. In embodiments, the hydroxytyrosol is sourced from an olive extract and the 3-O-acetyl-11-keto-β-boswellic acid is sourced from a *Boswellia serrata* extract. The composition may be formulated for oral administration to a mammalian subject, which may be selected from the group consisting of a human, dog, cat, horse, camel, or cow. In other embodiments, the composition may be formulated for oral administration to an avian subject.

In embodiments, the composition formulated for oral administration to a human subject may comprise 3-O-acetyl-11-keto-β-boswellic acid in an amount of from about 0.67 to about 2.70 mg per kg bodyweight and hydroxytyrosol in an amount of from about 0.15 to about 2.50 mg per kg bodyweight. In embodiments, the composition formulated for oral administration to a dog subject may comprise 3-O-acetyl-11-keto-β-boswellic acid in an amount of from about 1.24 to about 4.98 mg per kg bodyweight and hydroxytyrosol in an amount of from about 0.28 to about 4.60 mg per kg bodyweight.

In another aspect, the present disclosure provides a method of treating, repairing, or reducing damage to connective tissue caused by one or more inflammatory mediators, comprising administering to a mammalian or avian subject in need thereof an orally administrable composition comprising a synergistic combination of hydroxytyrosol and 3-O-acetyl-11-keto-β-boswellic acid as described above.

In yet another aspect, the present disclosure provides a method of reducing levels of one or more inflammatory mediators in connective tissue, comprising administering to a mammalian or avian subject in need thereof an orally administrable composition comprising a synergistic combination of hydroxytyrosol and 3-O-acetyl-11-keto-β-boswellic acid as described above.

In the following description, there are shown and described embodiments of the disclosed compositions and methods. As it should be realized, the described compositions and methods are capable of other, different embodiments and its several details are capable of modification in various, obvious aspects all without departing from the subject matter set forth and described in the following claims. Accordingly, the drawings and descriptions should be regarded as illustrative in nature and not as restrictive.

BRIEF DESCRIPTION OF THE DRAWINGS

The accompanying drawing figures incorporated herein and forming a part of the specification, illustrate several aspects of the disclosed compositions and together with the description serve to explain certain principles thereof. In the drawing.

Figure 1:
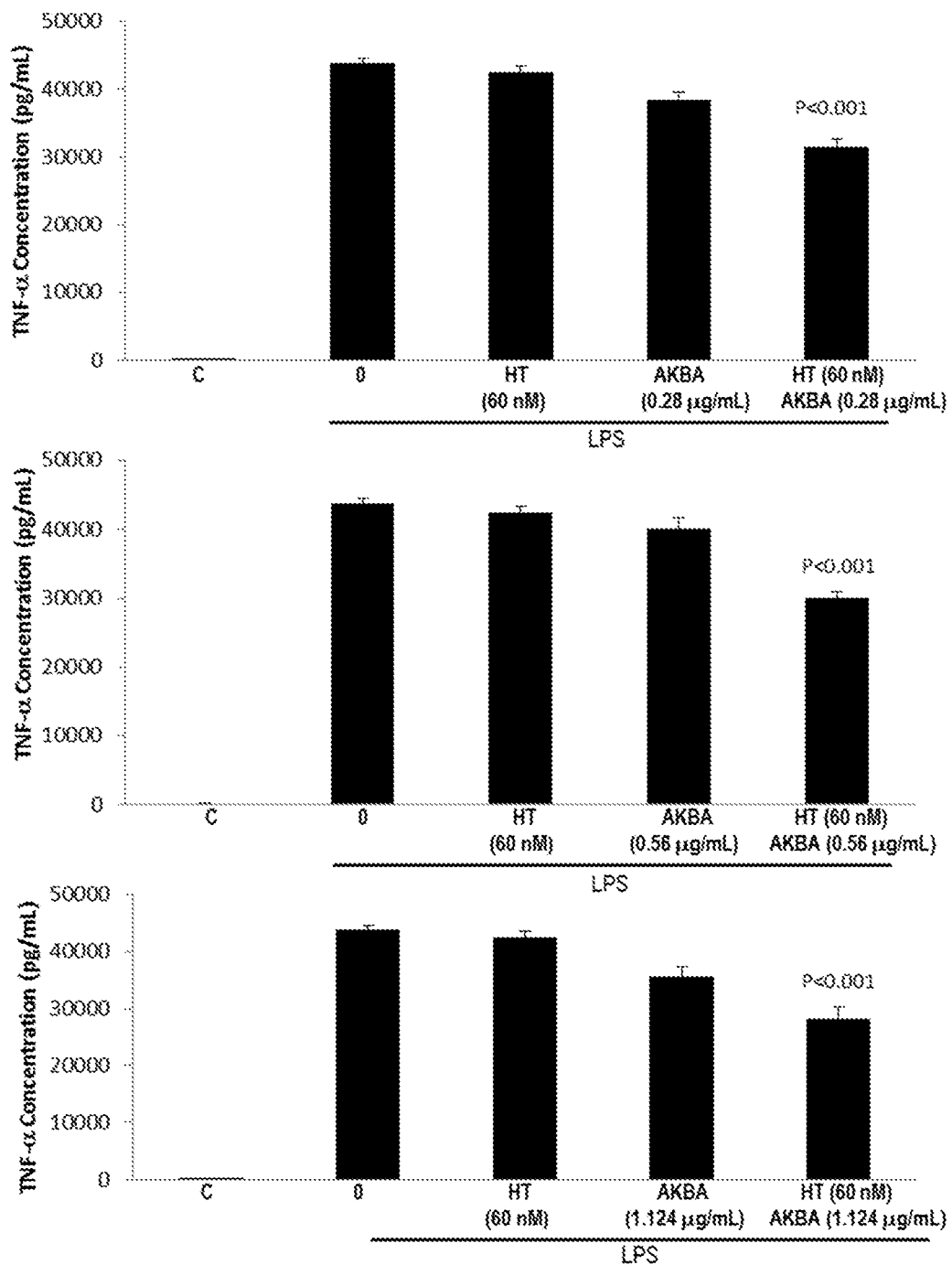
FIG. 1 illustrates the effect of hydroxytyrosol and AKBA in certain concentrations on TNF-α production in lipopolysaccharide-stimulated RAW 264.7 mouse macrophage cells.

Reference will now be made in detail to embodiments of the disclosed compositions and associated methods, examples of which are illustrated in the accompanying drawing figures.

DETAILED DESCRIPTION

The present invention provides for methods comprising administration of (i) 3-O-acetyl-11-keto-β-boswellic acid (AKBA) and (ii) hydroxytyrosol, to a mammalian or avian subject. AKBA and hydroxytyrosol may be administered together in one composition or dosage form, or they may be administered separately. In certain embodiments, AKBA and hydroxytyrosol are administered together in one composition or dosage form, or separately, within a period in which their therapeutic properties overlap. In embodiments, the compositions are administered separately within 1 hour. In other embodiments, the compositions are administered separately within 30 minutes. In still other embodiments, the compositions are administered separately within 5 minutes.

The term "mammalian subject" is any mammal, including, but not limited to humans, dogs, cats, horses, cows, and camels. The term "avian subject" refers to birds.

Hydroxytyrosol is a type of phenolic phytochemical found in parts of the olive tree. Hydroxytyrosol has an IUPAC name of 4-(2-Hydroxyethyl)-1,2-benzenediol and refers to a compound having the following structure:

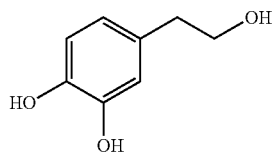 [SMILES: OCCc1ccc(O)c(O)c1]

As used herein, hydroxytyrosol may be of either synthetic origin or obtainable from natural sources such as from products and by-products derived from the olive tree by extraction and/or purification. Additionally, hydroxytyrosol may be administered in the form of hydroxytyrosol-comprising extracts obtainable from products and by-products derived from the olive tree. Products and by-products of olive trees encompass olives, olive tree leafs, olive pulps, olive oil, olive-derived vegetation water and olive oil dregs without being limited thereto. Based on the extraction procedure the amount, and respectively the ratio of the hydroxytyrosol, can be easily adjusted by a person skilled in the art. In embodiments, the hydroxytyrosol is derived from olives that may be obtained from conventional and commercially available sources such as growers.

The hydroxytyrosol employed herein can be prepared by a number of methods known in the art. The olives may be processed by any suitable means to obtain the compositions described. For example, the olives and/or olive leaves may be pressed to obtain a mixture including olive oil, vegetation water and solid byproducts. The hydroxytyrosol may be obtained directly from the mixture or the mixture may be fractionated and/or purified to obtain the hydroxytyrosol. The compositions may be fractionated and/or purified by a number of methods known to the person skilled in the art. Examples of fractionating methods include partitioning with an organic solvent, chromatography, high pressure liquid chromatography (HPLC), or the use of supercritical fluids.

Examples of references that deal with the extraction of hydroxytyrosol from olive leaves are WO02/18310 A1, US 2002/0198415 A1, WO2004/005228 A1, U.S. Pat. No. 6,416,808 and US 2002/0058078 A1 which disclose a method for acidic hydrolysis of olive vegetation water for 2 to 12 months until at least 90% of the present oleuropein has been converted. A method of extraction of hydroxytyrosol from olives, olive pulps, olive oil and oil mill waste water is described in U.S. Pat. No. 6,361,803 and WO01/45514 A1 and in US 2002/0004077 A1. EP 1 582 512 A1 describes an extraction of hydroxytyrosol from olive leaves. A method for obtaining hydroxytyrosol from the vegetation water of de-pitted olives is disclosed in US 2004/0039066 A1 in paragraphs [0080]-[0091]. Similarly suitable for use in the present invention are commercially available hydroxytyrosol-containing olive extracts.

The oral bioavailability of a single 2.5 mg/kg dose of hydroxytyrosol in human subjects has been reported in the literature, with an observed peak plasma concentration of 1.11±0.20 μmol/L. González-Santiago, et al., Pharmacological research, 61.4 (2010): 364-370. Dosage calculations can be determined by those of skilled in the art by evaluating body weight, surface area, and species differences. Similarly, dosages for cross-species extrapolation can be calculated by one skilled in the art using conventional dose conversion methods.

The typical dosage rate of hydroxytyrosol is about 0.001 mg/kg to about 2.0 mg/kg. In some embodiments, the typical daily dosage is at least 0.1 mg and up to 300 mg for human and non-human subjects. The daily dosage refers to the total dosage administered in a 24-hour period.

According to some exemplary embodiments, hydroxytyrosol may be administered at a dose of 0.15 to 2.50 mg per kg bodyweight of a human subject (i.e. 9-250 mg for a 60 kg human subject).

According to some exemplary embodiments, hydroxytyrosol may be administered at a dose of 0.28 to 4.60 mg per kg bodyweight of a dog subject (i.e. 2.8-46 mg for a 10 kg dog subject).

Hydroxytyrosol may be administered at a frequency of one time per week to five times daily. In embodiments, hydroxytyrosol is administered once every two days to three times daily. In alternative embodiments, hydroxytyrosol is administered one to two times daily. In still other embodiments, hydroxytyrosol is administered once daily. Hydroxytyrosol may be taken with or without the administration of food.

Phytochemicals extracted from *Boswellia serrata* have been reported to be active in the treatment of numerous afflictions and maladies. The gum resin of *Boswellia serrata* has long been in use for the treatment of rheumatoid arthritis and gout by the practitioners of Ayurvedic medicines in the Indian system of medicine. Various extracts of the gum resin have shown potent anti-inflammatory and anti-atherogenic activity in laboratory animals. The biological activity of the extract has been related to the components of the boswellic acid fraction. 3-O-acetyl-11-keto-β-boswellic acid (AKBA) has been identified as the most active compound in *Boswellia serrata* extracts. *Boswellia serrata* extracts containing AKBA have been reported to inhibit 5-lipoxygenase and matrix metalloproteinase-3 (MMP-3) in vitro, as described in WO2010/029578 A2. WO2010/029578 A2 similarly reports the anti-inflammatory efficacies of compositions comprising *Boswellia serrata* extract selectively enriched in AKBA to 30% in vivo, including significant reductions in the serum biomarkers TNF-α and IL-1 β.

The bioavailability of a single dose administration of 100 mg/kg dose of *Boswellia serrata* extract standardized to 30% AKBA in rat serum has been reported in the literature, with an observed peak serum concentration of 2.0 micrograms/mL being reported. Sengupta, et al. Molecular and cellular biochemistry, 354.1-2 (2011): 189-197. Dosage calculations can be determined by those of skilled in the art by evaluating body weight, surface area, and species differences. Similarly, dosages for cross-species extrapolation can be calculated by one skilled in the art using conventional dose conversion methods.

The typical dosage rate of AKBA is about 0.01 mg/kg to about 10.0 mg/kg. In some embodiments, the typical daily dosage is at least 1 mg and up to about 1 g for human and non-human subjects. The daily dosage refers to the total dosage administered in a 24-hour period.

According to some exemplary embodiments, AKBA may be administered at a dose of 0.67 to 2.70 mg per kg bodyweight of a human subject (i.e. 40-162 mg for a 60 kg human subject).

According to some exemplary embodiments, AKBA may be administered at a dose of 1.24 to 4.98 mg per kg bodyweight of a dog subject (i.e. 12.4-49.8 mg for a 10 kg dog subject).

AKBA may be administered at a frequency of one time per week to five times daily. In certain embodiments, AKBA is administered once every two days to three times daily. In alternative embodiments, AKBA is administered one to two times daily. In still other embodiments embodiments, AKBA is administered once daily. AKBA may be taken with or without the administration of food.

In some embodiments, the combination of (i) hydroxytyrosol and (ii) AKBA demonstrates synergy. Synergy refers to the effect wherein a combination of two or more components provides a result which is greater than the sum of the effects produced by the agents when used alone. In certain embodiments, the result is statistically significant and greater than the additive effect. In some embodiments, the combination of hydroxytyrosol and AKBA has a statistically significant, greater effect than each component alone. In certain embodiments, the combination of hydroxytyrosol and AKBA demonstrates synergy in one or more of the following: preventing, treating, repairing or reducing damage to connective tissues; reducing symptoms associated with damage to connective tissue in an avian or mammalian subject; and reducing levels of one or more inflammatory mediators in connective tissue.

The present invention provides a method of preventing, treating, repairing, reducing damage, or controlling inflammation of connective tissues, protecting cartilage, or reducing symptoms associated with damage to connective tissue in an avian or mammalian subject, comprising administering to the subject: (i) hydroxytyrosol and (ii) AKBA. The term "connective tissue" includes but not limited to cartilage, bone, synovium, ligament, meniscus, and tendon. In some embodiments, the administration of (i) hydroxytyrosol and (ii) AKBA may prevent, treat, repair or reduce damage to connective tissues. The damage to connective tissue may be a result of physical injury or may represent "wear and tear" from continual use, weight and age, for example, from osteoarthritis. Damage to connective tissue may also result from disease such as rheumatoid arthritis, synovial disorders, infection related rheumatic diseases and inflammatory connective tissue disorders. In some embodiments, the administration of (i) hydroxytyrosol and (ii) AKBA may reduce symptoms associated with damage to connective tissue in an avian or mammalian subject. Symptoms associated with damage to connective tissue include, but are not limited to: pain, discomfort, pressure, inflammation, stiffness and/or swelling.

The present invention also provides a method of reducing levels of one or more inflammatory mediators in connective tissue, comprising administering to an avian or mammalian subject: (i) hydroxytyrosol and (ii) AKBA. The inflammatory mediators include, but are not limited to tumor necrosis factor-α (TNF-α), prostaglandins such as prostaglandin $E_2$ ($PGE_2$), cytokines such as interleukin-1β (IL-1β) and, chemokines, leukotrienes, nitric oxide, and reactive oxygen species.

The administration of hydroxytyrosol and AKBA may also be useful for treating, preventing, and reducing damage or reducing symptoms associated with conditions affecting the cardiovascular system, nervous system, musculoskeletal system and gastrointestinal system. In one aspect, the present disclosure provides compositions and methods for preventing and/or reducing an inflammatory response and/or inflammation in a subject. In one aspect, the present disclosure provides compositions and methods for managing inflammatory disorders or generally reducing inflammatory burden of a human or non-human animal. Accordingly, in one embodiment, the present invention provides a method of preventing and/or reducing an inflammatory response and/or inflammation in one or more tissues, the method including delivering to the one or more tissues the compositions of the present invention.

The present invention also provides for an orally administrable composition comprising: (i) hydroxytyrosol and (ii) AKBA. The orally administrable composition is any dosage form which can be administered orally, such as, but not limited to: a capsule, a tablet, a powder that can be dispersed in a beverage, a paste, in pelletized form, a liquid such as a solution, suspension, or emulsion, a soft gel/chew capsule, a chewable bar or other convenient dosage form such as oral liquid in a capsule, as known in the art.

The orally administrable composition may contain one or more non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients may be pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

The orally administrable compositions may further comprise one or more active ingredients. For example, the compositions may further comprise one or more drugs or nutritional supplements. In some embodiments, the compositions may further comprise compounds which are beneficial to connective tissue. Example include, but are not limited to glycosaminoglycans such as chondroitin, aminosugars such as glucosamine, methylsulfonylmethane (MSM), collagen (including collagen type II), green tea extracts, scutellaria extracts, acacia extracts, turmeric extracts, curcumin, cetyl myristoleate complex (CMO) and egg shell membrane.

All references cited herein are incorporated by reference in their entirety.

EXAMPLES

Example 1: Effect of Hydroxytyrosol and AKBA on TNF-α Production in Lipopolysaccharide (LPS) Stimulated RAW 264.7 Mouse Macrophage Cells RAW 264.7 mouse macrophage cells were pre-treated with 60 nM, 160 nM, or 1 µM hydroxytyrosol (HT) (98% purity, Sigma-Aldrich, St. Louis, Mo.) alone, 0.28 µg/mL, 0.56 µg/mL or 1.124 µg/mL AKBA (administered as 5-LOXIN®, standardized to 30% AKBA, PLT Health Solutions, Inc.) alone, or each of the three concentrations of HT combined with each of the three concentrations of AKBA for 24 hours. Cells were then stimulated for an additional 24 hours with 1 µg/mL lipopolysaccharide (LPS). LPS is an endotoxin in the bacterial cell wall capable of inducing an inflammatory response which includes an increased production of TNF-α. Cellular supernatants were analyzed for TNF-α production. Statistical comparisons were made using one-way analysis of variance (ANOVA) and Tukey post-hoc analysis was performed where differences of $P<0.05$ were considered significant. Data is presented as the mean+/−1 SD.

Figure 2:
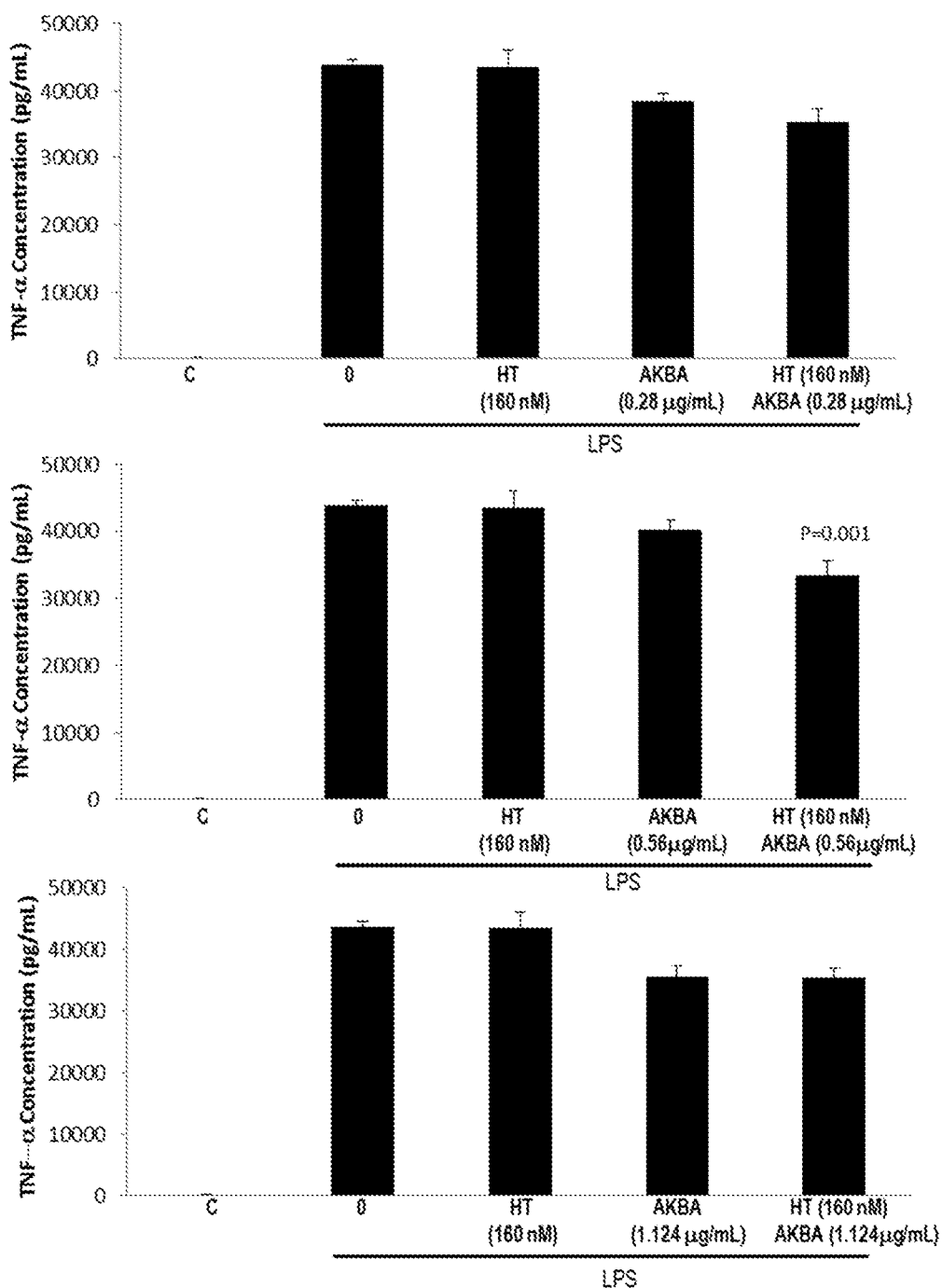
FIG. 2 illustrates the effect of hydroxytyrosol and AKBA in certain concentrations on TNF-α production in lipopolysaccharide-stimulated RAW 264.7 mouse macrophage cells.
Figure 3:
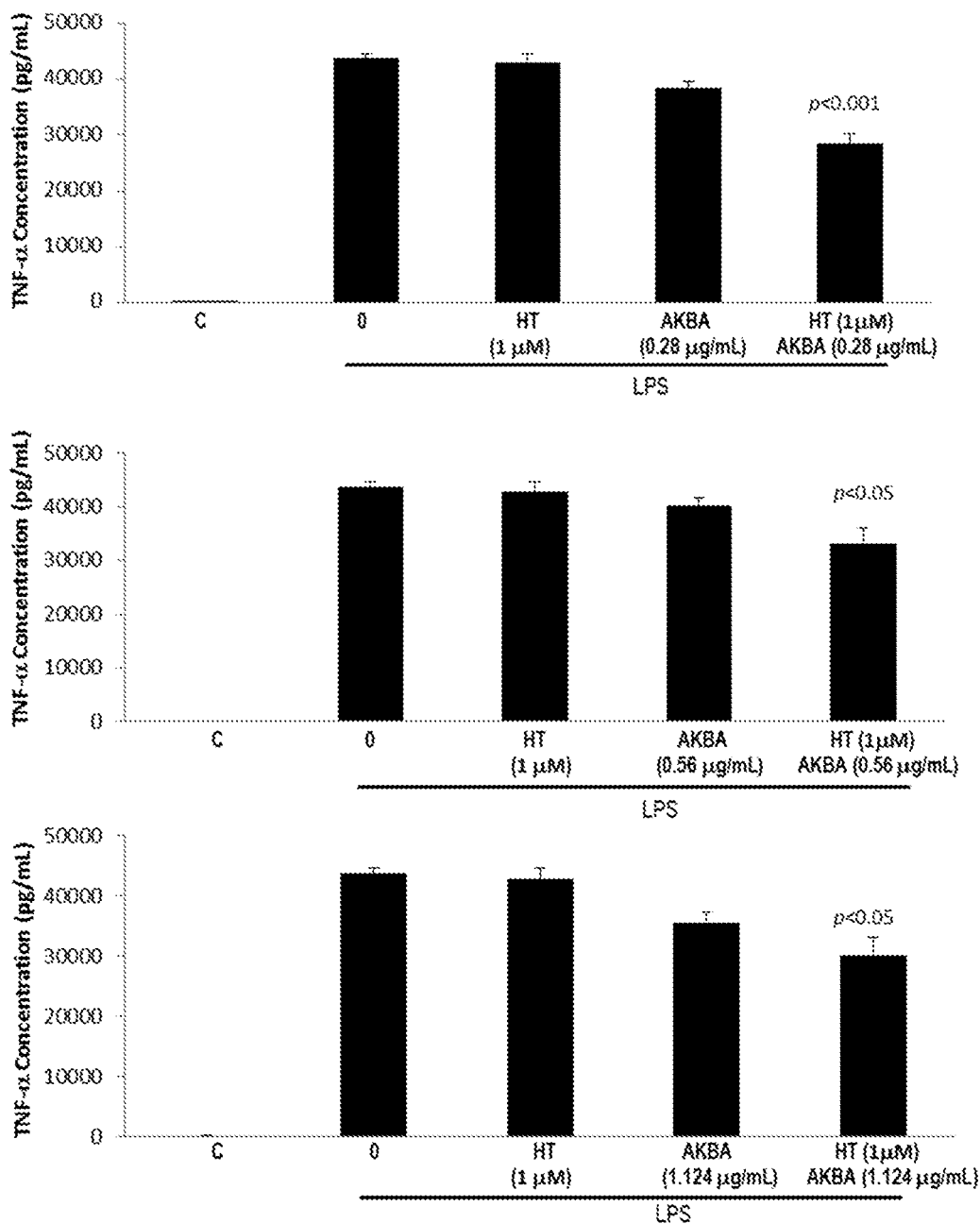
FIG. 3 illustrates the effect of hydroxytyrosol and AKBA in certain concentrations on TNF-α production in lipopolysaccharide-stimulated RAW 264.7 mouse macrophage cells.

Statistically significant greater reductions in the levels of TNF-α were observed when each of the three concentrations of HT were combined with AKBA compared to the reduction by either agent alone. The combination of 60 nM HT with either 0.28 µg/mL, 0.56 µg/mL, or 1.124 µg/mL AKBA resulted in a greater reduction of TNF-α production than either HT ($P<0.001$) or AKBA ($P<0.001$) alone (FIG. 1). Statistical significance was reached in the reduction of TNF-α in cells treated with 160 nM HT in combination with 0.56 µg/mL AKBA compared with either HT ($P<0.001$) or AKBA ($P=0.001$) alone (FIG. 2). The treatment of cells with 1 µM HT and either 0.28 µg/mL, 0.56 µg/mL, or 1.124 µg/mL AKBA also resulted in statistical significant reductions compared to HT alone ($P<0.001$, $P=0.002$ and $P<0.001$, respectively) and AKBA alone ($P<0.001$, $P=0.02$ and $P=0.004$, respectively) (FIG. 3).

What is claimed:

1. A composition, comprising hydroxytyrosol and 3-O-acetyl-11-keto-β-boswellic acid provided in an amount effective to prevent or reduce an inflammatory response in connective tissue of a subject in need thereof.

2. The composition of claim 1, wherein the hydroxytyrosol is sourced from an olive extract.

3. The composition of claim 1, wherein the 3-O-acetyl-11-keto-β-boswellic acid is sourced from a *Boswellia serrata* extract.

4. The composition of claim 1, formulated for oral administration to a mammalian subject or an avian subject.

5. The composition of claim 4, wherein the mammalian subject is selected from the group consisting of a human, dog, cat, horse, camel, or cow.

6. The composition of claim 5, wherein the composition formulated for oral administration to the human subject comprises 3-O-acetyl-11-keto-β-boswellic acid in an amount of from about 0.8 to about 2.50 mg per kg bodyweight.

7. The composition of claim 5, wherein the composition formulated for oral administration to the dog subject comprises 3-O-acetyl-11-keto-β-boswellic acid in an amount of from about 1.4 to about 4.50 mg per kg bodyweight.

8. The composition of claim 5, wherein the composition formulated for oral administration to the human subject comprises hydroxytyrosol in an amount of from about 0.2 to about 2 mg per kg bodyweight.

9. The composition of claim 5, wherein the composition formulated for oral administration to the dog subject comprises hydroxytyrosol in an amount of from about 0.4 to about 4 mg per kg bodyweight.

10. The composition of claim 1, wherein the inflammatory response is mediated by one or more of tumor necrosis factor alpha, prostaglandin $E_2$, cyclooxygenase-2, and nitric oxide.

* * * * *